(12) United States Patent
Doi

(10) Patent No.: US 10,118,025 B2
(45) Date of Patent: Nov. 6, 2018

(54) BALLOON CATHETER AND MANUFACTURING METHOD OF BALLOON CATHETER

(71) Applicant: TERUMO KABUSHIKI KAISHA, Tokyo (JP)

(72) Inventor: Yuta Doi, Fujinomiya (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 405 days.

(21) Appl. No.: 14/872,693

(22) Filed: Oct. 1, 2015

(65) Prior Publication Data

US 2016/0022969 A1 Jan. 28, 2016

Related U.S. Application Data

(63) Continuation of application No. PCT/JP2014/056791, filed on Mar. 13, 2014.

(30) Foreign Application Priority Data

Apr. 2, 2013 (JP) .................................. 2013-076898

(51) Int. Cl.
*A61M 29/00* (2006.01)
*A61M 31/00* (2006.01)
(Continued)

(52) U.S. Cl.
CPC ...... *A61M 25/10186* (2013.11); *A61M 25/10* (2013.01); *A61M 25/104* (2013.01);
(Continued)

(58) Field of Classification Search
CPC .. A61M 2025/1031; A61M 2025/1093; A61M 25/0054; A61M 25/10;
(Continued)

(56) References Cited

U.S. PATENT DOCUMENTS

| 4,932,959 A | 6/1990 | Horzewski et al. |
| 5,360,403 A | 11/1994 | Mische |

(Continued)

FOREIGN PATENT DOCUMENTS

| JP | 2-271874 A | 11/1990 |
| JP | H 0584309 A | 4/1993 |

(Continued)

OTHER PUBLICATIONS

International Search Report (PCT/ISA/210) dated Apr. 15, 2014, by the Japanese Patent Office as the International Searching Authority for International Application No. PCT/JP2014/056791.

(Continued)

*Primary Examiner* — Jason Flick

(74) *Attorney, Agent, or Firm* — Buchanan Ingersoll & Rooney PC

(57) ABSTRACT

A balloon catheter which can rather smoothly move inside living body organs, and can improve trackability and pushability. The balloon catheter has an inner shaft that includes a guidewire lumen into which a guidewire can be inserted, an outer shaft that forms a fluid lumen for introducing a fluid on an outer periphery of the inner shaft, a membranous material that causes a space portion into which the fluid can flow to communicate with the fluid lumen, and that partitions the space portion on the outer periphery of the distal portion side of the inner shaft, and an inflatable and deflatable balloon in which a lumen into which the fluid can flow is formed on an outer periphery of the membranous material.

15 Claims, 8 Drawing Sheets

(51) Int. Cl.
*A61M 25/10* (2013.01)
*A61M 25/00* (2006.01)

(52) U.S. Cl.
CPC .... *A61M 25/1027* (2013.01); *A61M 25/1029* (2013.01); *A61M 25/0054* (2013.01); *A61M 25/1034* (2013.01); *A61M 2025/1031* (2013.01); *A61M 2025/1093* (2013.01)

(58) Field of Classification Search
CPC ........ A61M 25/10186; A61M 25/1027; A61M 25/1029; A61M 25/1034; A61M 25/104
USPC ...................................................... 604/99.03
See application file for complete search history.

(56) References Cited

U.S. PATENT DOCUMENTS

| | | | |
|---|---|---|---|
| 5,496,275 A | 3/1996 | Sirhan et al. | |
| 6,129,705 A * | 10/2000 | Grantz | A61F 2/82 604/103.02 |
| 8,348,890 B2 * | 1/2013 | Gerrans | A61M 25/1011 604/101.02 |
| 2003/0028234 A1 | 2/2003 | Miller et al. | |
| 2010/0125244 A1 * | 5/2010 | McAndrew | A61M 25/10 604/98.01 |
| 2012/0116490 A1 * | 5/2012 | Wesselmann | A61F 2/958 623/1.11 |

FOREIGN PATENT DOCUMENTS

| | | |
|---|---|---|
| JP | 6-233822 A | 8/1994 |
| JP | 11-169464 A | 6/1999 |
| JP | 2002-291897 A | 10/2002 |
| JP | 2004-537378 A | 12/2004 |
| JP | 2008 148887 A | 7/2008 |
| JP | 2010-124955 A | 6/2010 |

OTHER PUBLICATIONS

Office Action (Notification of Reasons for Refusal) dated Aug. 29, 2017, by the Japanese Patent Office in Japanese Patent Application No. 2015-509976, and an English Translation of the Office Action. (6 pages).

* cited by examiner

BALLOON CATHETER AND MANUFACTURING METHOD OF BALLOON CATHETER

CROSS-REFERENCES TO RELATED APPLICATIONS

This application is a continuation of International Application No. PCT/JP2014/056791 filed on Mar. 13, 2014, and claims priority to Japanese Application No. 2013-076898 filed on Apr. 2, 2013, the entire content of both of which is incorporated herein by reference.

TECHNICAL FIELD

The present invention generally relates to a balloon catheter and to a manufacturing method of a balloon catheter in a medical field.

BACKGROUND DISCUSSION

As procedures for expanding a stenosis formed in living body blood vessels, so-called percutaneous transluminal angioplasty (PTA) or percutaneous transluminal coronary angioplasty (PTCA) which is performed by using a balloon catheter is widely known. In the procedures using the balloon catheter, an operation inserting a guidewire into a stenosis is carried out first. Subsequently, an operator's hand operates the balloon catheter so as to be guided by the guidewire, thereby pushing the overall balloon catheter and inserting a balloon into the stenosis. Thereafter, the stenosis (treating area) is spread out by inflating the balloon, thereby restoring a blood flow therein.

The balloon catheter includes the balloon to which a fluid serving as a pressurizing medium is injected, an inner tube into which the guidewire is inserted in order to guide the balloon catheter to the stenosis, and an outer tube which forms a lumen capable of injecting the fluid between the inner tube and the outer tube. The inner tube and the outer tube are configured to generally include a thin and flexible elongated member which is improved in order to follow living body organs or the like (for example, blood vessels) which are curved and thin. An example of a balloon catheter is disclosed in Japanese Application Publication No. 2002-291897.

SUMMARY

According to the conventional balloon catheter configured as described above, movement itself of the balloon catheter can be smoothly performed inside the living body organs. However, due to a configuration of the inner tube and the outer tube, trackability or pushability becomes poor. Consequently, it is difficult to insert the balloon into the stenosis by performing an operation of pushing the balloon catheter from the operator's hand side.

The balloon catheter disclosed here can smoothly move inside living body organs, and is configured to improve trackability and pushability.

A balloon catheter includes: an inner shaft that includes a guidewire lumen configured to receive a guidewire so that the balloon catheter can be guided along the guidewire; an outer shaft that forms, together with the inner shaft, a fluid lumen into which a fluid is to be introduced; a membranous material that defines, together with the inner shaft, a space portion located outwardly of an outer periphery of a distal portion of the inner shaft; an inflatable and deflatable balloon in which a lumen is formed, the balloon being located outwardly of an outer periphery of the membranous material; the membranous material including an ejection portion which permits the fluid in the space portion to flow into the lumen of the balloon when an internal pressure in the space portion increases to a predetermined pressure as the fluid flows into the space portion; and the inner shaft including a contracting and transforming portion which transforms at least a portion of the inner shaft so as to contract radially inward in response to an increase in the internal pressure in the space portion.

A distal portion side of the outer shaft is arranged so as to cover the inner shaft within a predetermined range in an axial direction. A proximal portion side of the membranous material is arranged on an outer periphery of the distal portion side of the outer shaft. A proximal portion side of the balloon is arranged on an outer periphery of the proximal portion side of the membranous material.

A proximal portion of the membranous material is fixed to an outer peripheral surface on the distal portion side of the outer shaft. A proximal portion of the balloon is fixed to an outer peripheral surface of the outer shaft at a position on the proximal portion side in the axial direction relative to the proximal portion of the membranous material.

The ejection portion has a fragile portion which forms an opening in the membranous material by rupturing a portion of the membranous material over a predetermined range in the axial direction.

Another aspect involves a method of manufacturing a balloon catheter. The balloon catheter includes: an inner shaft into which a guidewire is insertable, an outer shaft positioned outwardly of on an outer periphery of the inner shaft, a membranous material positioned outwardly of an outer periphery of a distal portion of the inner shaft to form a space portion between the distal portion of the inner shaft and the membranous material, and a balloon positioned outwardly of an outer periphery of the membranous material to define a lumen between the balloon and the membranous material, at least a part of the inner shaft being transformable so as to contract radially inward in response to an increase in internal pressure in the space portion. The method comprises: sealing one opening portion of a first tube material in a state in which a second tube material forming the membranous material is positioned inside the first tube material forming the balloon, with the one opening portion of the first tube material being either a proximal opening portion at a proximal end of the first tube material or a distal opening portion at a distal end of the first tube material, and with the first tube material possessing an other opening portion at an end of the first tube opposite to the one opening portion. The method also involves discharging gas between the first tube material and the second tube material via the other opening portion which is not sealed; sealing the other opening portion of the first tube material; and joining the first tube material and the second tube material to a shaft assembly which includes the inner shaft and the outer shaft.

According to the balloon catheter disclosed here, the inner shaft is contracted, and is brought into pressure contact with the guidewire. Accordingly, the balloon catheter is enabled to perform forward and rearward movement or the like in a state where the balloon catheter is allowed to have improved trackability and pushability. In addition, the balloon catheter can be smoothly moved along living body organs or the like by releasing a state where the inner shaft is in pressure contact with the guidewire. Furthermore, the fluid can be caused to flow into the lumen of the balloon from the space portion by increasing the internal pressure in the space portion up to the predetermined pressure. Accordingly, it is possible to perform various operations such as press contact between the inner shaft and the guidewire, releasing the press contact, and inflating the balloon, by adjusting a flow rate of the fluid which is caused to flow into the space portion.

The balloon catheter is also configured so that it is possible to rather simply and easily carry out assembly work of the balloon catheter.

The proximal portion of the membranous material is covered with the proximal portion of the balloon, and so it is possible to preferably prevent the fluid from leaking out from the proximal portion side of the membranous material.

The opening is formed in the membranous material over a relatively wide range along the axial direction by using the fragile portion included in the membranous material. Therefore, the fluid can be caused to smoothly flow into the lumen of the balloon from the space portion, and thus it is possible to preferably prevent the fluid from staying in the space portion after the fluid is caused to flow out.

The manufacturing method of a balloon catheter uses configuration members which are the first tube material forming the balloon in which the lumen is formed on the outer periphery of the membranous material and the second tube material forming the membranous material which partitions the space portion into which the fluid can flow on the outer periphery of the inner shaft.

According to another aspect, a method of using a balloon catheter comprises inserting a balloon catheter into a living body organ, with the balloon catheter comprising: an inner shaft that includes a guidewire lumen, an outer shaft positioned outwardly of the inner shaft, a membranous material positioned outwardly of the inner shaft, and an inflatable and deflatable balloon located outwardly of the membranous material, the membranous material possessing an inner peripheral surface and the inner shaft possessing an outer peripheral surface. The method also involves: moving the balloon catheter in the living body organ by guiding the balloon catheter along a guidewire located in the guidewire lumen to move the balloon catheter relative to the guidewire within the living body organ; introducing fluid into a space between the outer peripheral surface of the inner shaft and the inner peripheral surface of the membranous material to cause a portion of the inner shaft to deform inwardly into contact with the guidewire in the guidewire lumen so that the guidewire and the balloon catheter move together as a unit; moving the balloon catheter while the portion of the inner shaft is in contact with the guidewire to move the guidewire and the balloon catheter together and position the balloon catheter at a stenosis; and inflating the balloon into contact with the stenosis to spread out the stenosis.

DETAILED DESCRIPTION

Figure 1:
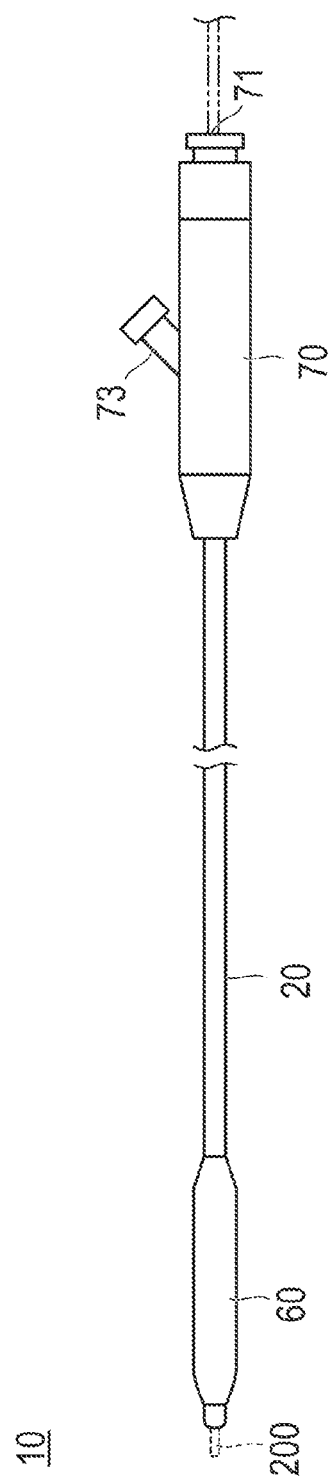
FIG. 1 is a plan view illustrating an overall configuration of a balloon catheter according to an embodiment disclosed here.

Hereinafter, an embodiment of a balloon catheter representing one example of the inventive balloon catheter disclosed here will be described with reference to the drawings. In some cases, dimensional proportions in the drawings may be exaggerated for convenience of description and may differ from actual proportions.

FIGS. 1 to 5 illustrate a configuration of each unit of a balloon catheter 10 according to one embodiment disclosed here. FIGS. 6 to 9 are views provided for describing an operation of the balloon catheter 10 according to the embodiment. In the following description, the left side in each drawing is referred to as a "distal side", "distal end" or "distal portion", and the right side is referred to as a "proximal side", "proximal end" or "proximal portion".

As illustrated in FIG. 1, the balloon catheter 10 includes an elongated shaft assembly 20, a balloon 60 which is disposed on the distal side or distal end of the shaft assembly 20, and a hub 70 serving as a hand operation unit which is disposed on the proximal side or proximal end of the shaft assembly 20.

The balloon catheter 10 according to the present embodiment is a so-called PTCA inflatable catheter for treating a stenosis in which the shaft assembly 30 is inserted into living body organs, for example, coronary arteries and the balloon 60 disposed on the distal side is inflated in the stenosis (lesion) so as to spread out the stenosis. However, the present invention is applicable to catheters in addition to the above-described PTCA inflatable catheter. For example, the present invention is applicable to catheters which are used to treat and improve the stenosis formed in other living body organs such as other blood vessels, biliary ducts, bronchial tubes, esophagi, urethrae, other viscera, and the like.

In addition, in the present embodiment, a balloon catheter which is a so-called over-the-wire type will be described as an example in which a guidewire 200 can be inserted into the balloon catheter 10 through an opening portion 71 of the hub 70 disposed on the proximal side of the shaft assembly 30. However, the present invention is also applicable to other types, for example, a balloon catheter which is a so-called rapid exchange type in which the guidewire is obliquely inserted from a substantially intermediate portion of the shaft assembly.

Hereinafter, the configuration of each part of the balloon catheter 10 will be described in detail.

Figure 2:
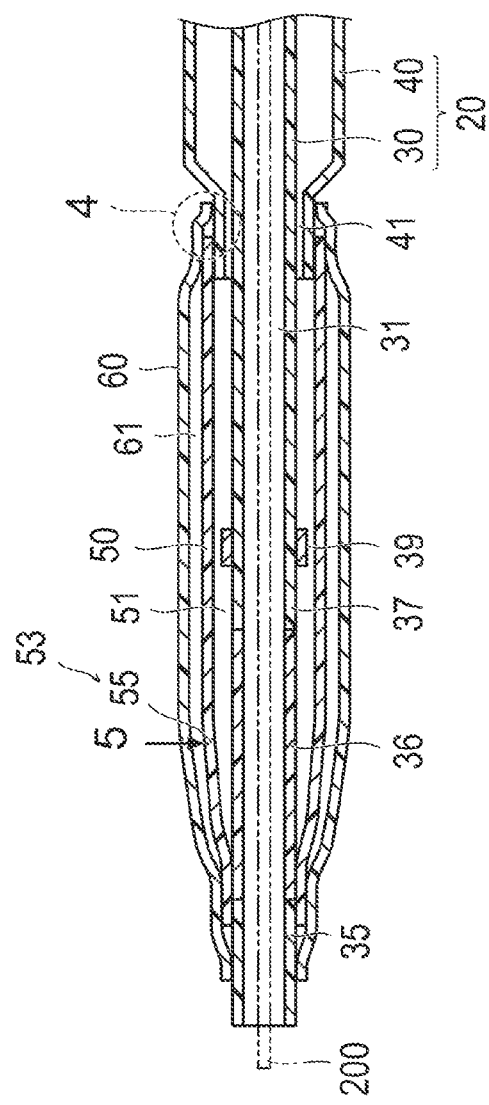
FIG. 2 is an enlarged view illustrating a cross-section on a distal portion side of the balloon catheter according to the embodiment.

As illustrated in FIG. 2, the balloon catheter 10 has an inner shaft 30 including a guidewire lumen 31 into which the guidewire 200 is inserted, an outer shaft 40 that together with the outer periphery of the inner shaft 30 forms a fluid lumen 41 permitting injection or introduction of a fluid, a membranous material 50 that defines, together with the inner shaft 30, a space portion 51 located outwardly of an outer periphery of a distal portion of the inner shaft 30, and an inflatable and deflatable balloon 60 is formed, the balloon 30 is located outwardly of an outer periphery of the membranous material 50.

Figure 8:
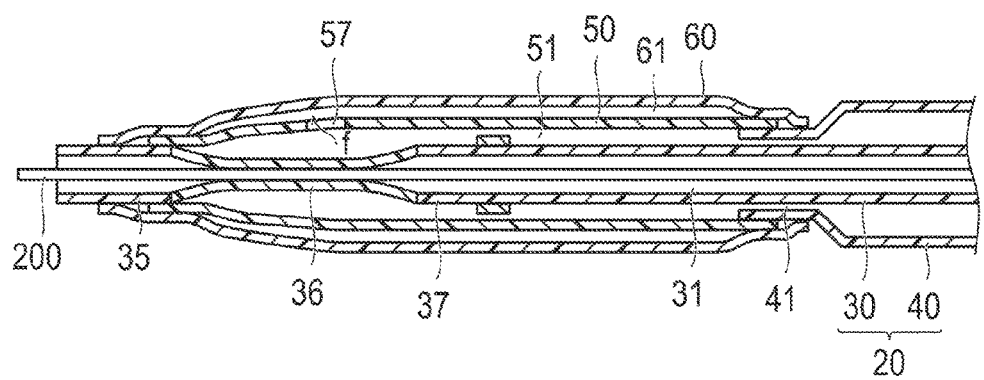
FIG. 8 is a cross-sectional view for describing an operation of the balloon catheter according to the embodiment.
Figure 9:
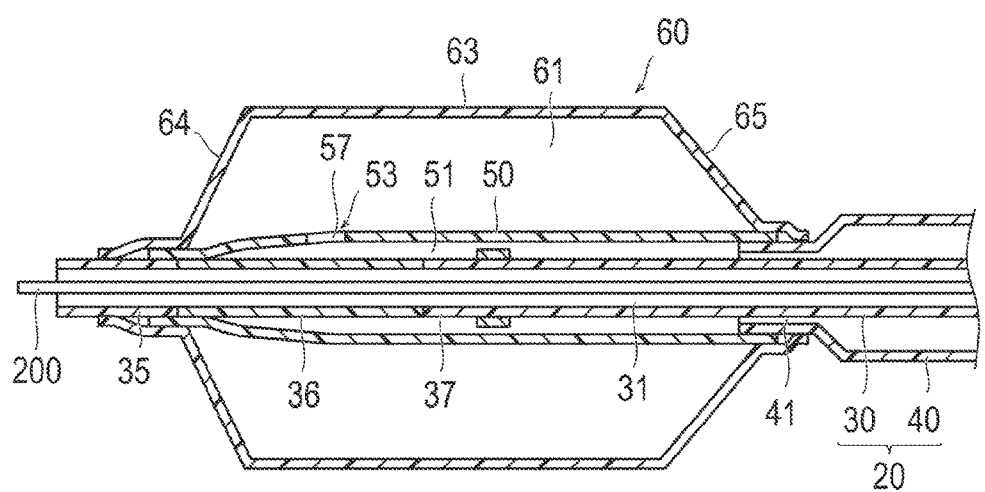
FIG. 9 is a cross-sectional view for describing an operation of the balloon catheter according to the embodiment.

As illustrated in FIG. 9, the membranous material 50 has an ejection portion 53 which causes the fluid to flow from the space portion 51 to the lumen 61 of the balloon 60, when internal pressure in the space portion 51 increases up to a predetermined pressure as the fluid flows into the space portion 51. In addition, as illustrated in FIG. 8, the inner shaft 30 has a contracting and transforming portion 36 which transforms at least a portion of the inner shaft 30 so as to contract radially inward in accordance with an increase in the internal pressure in the space portion 51. Then, in the contracted portion of the inner shaft 30, the contracting and transforming enable the inner shaft 30 to come into pressing contact with the guidewire 200 which is positioned in the guidewire lumen 31 of the inner shaft 30.

Figure 3:
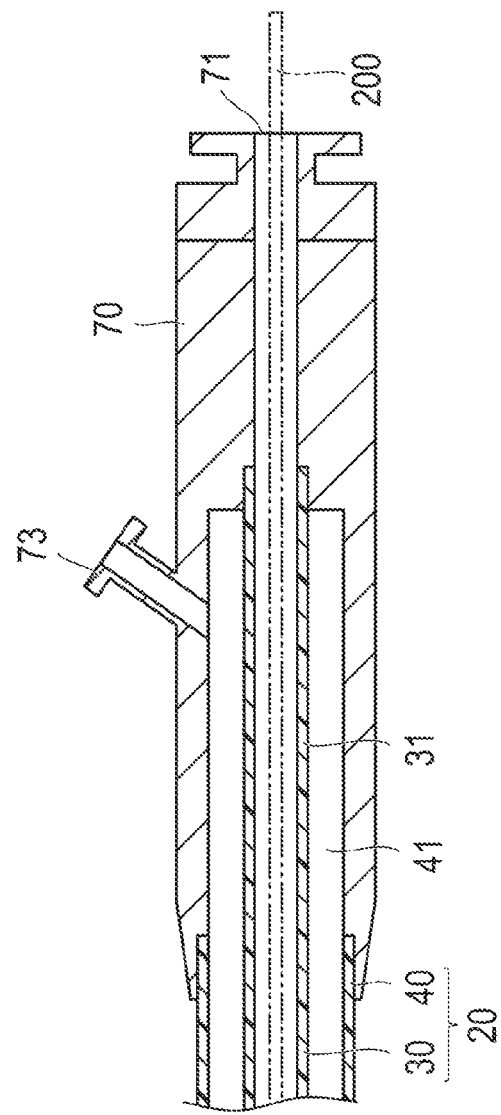
FIG. 3 is an enlarged view illustrating a cross-section on an operators hand side of the balloon catheter according to the embodiment.

As illustrated in FIGS. 2 and 3, the shaft assembly 20 is configured to include the flexible inner shaft 30 and the flexible outer shaft 40. The flexible outer shaft 40 is arranged coaxially with the inner shaft 30 and is disposed at a position where the distal end of the flexible outer shaft 40 is located rearward relative to or proximal of the distal end of the inner shaft 30 by a predetermined length. The proximal end of the inner shaft 30 and the proximal end of the outer shaft 40 are respectively and fixedly attached to predetermined portions of the hub 70.

The guidewire lumen 31 of the inner shaft 30 communicates with an opening portion 71 disposed in the proximal end of the hub 70. The fluid lumen 41 configured to introduce or inject the fluid serving as a pressurizing medium for inflating the balloon 60 is formed between the outer surface of the inner shaft 30 and the inner surface of the outer shaft 40, and between the outer surface of the inner shaft 30 and the hub 70. The fluid lumen 41 communicates with a port 73 which is disposed in the hub 70, and the space portion 51 which is partitioned between the inner shaft 30 and the membranous material 50. Therefore, the fluid supplied via the port 73 flows into the space portion 51. As described above, after an opening 57 is formed in the space portion 51, the fluid flows into the lumen 61 of the balloon 60 via the opening 57 (refer to FIGS. 8 and 9).

A fluid tube connected to a fluid supply source for supplying the fluid can be connected to the port 73 disposed in the hub 70 in liquid-tight and air-tight manners.

In the balloon catheter 10, the space portion 51 is positioned between the outer periphery of the inner shaft 30 and the inner periphery of the membranous material 50, and the lumen 61 of the balloon 60 is positioned between the outer periphery of the membranous material 50 and the inner periphery of the balloon 60. In order to easily manufacture the balloon catheter 10 having this configuration, for example, it is possible to configure each member as follows.

Figure 4:
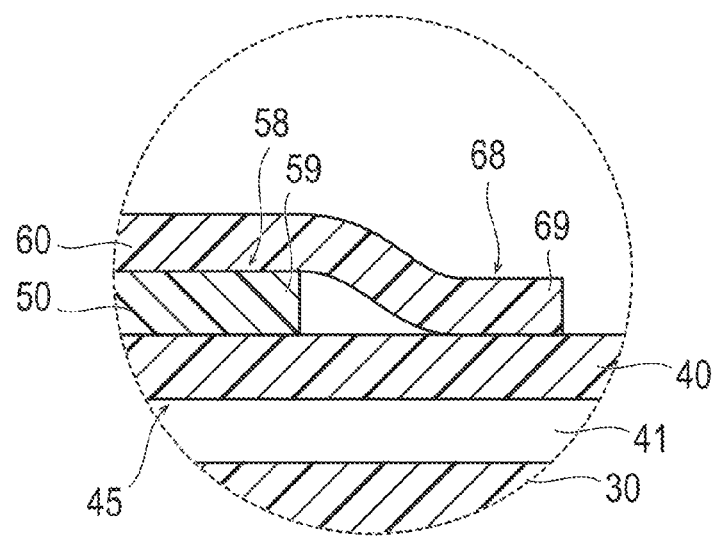
FIG. 4 is an enlarged cross-sectional view illustrating a broken line portion 4 illustrated in FIG. 2.

As illustrated in FIGS. 2 and 4, a distal portion 45 of the outer shaft 40 is arranged to cover the inner shaft 30 over a predetermined range in the axial direction. In addition, a proximal portion 58 of the membranous material 50 is arranged on the outer periphery of the distal portion 45 of the outer shaft 40, and a proximal portion 68 of the balloon 60 is arranged on the outer periphery of the proximal portion 58 of the membranous material 50. According to this arrangement, it is possible to manufacture the balloon catheter 10 according to the following procedure.

Figure 12:
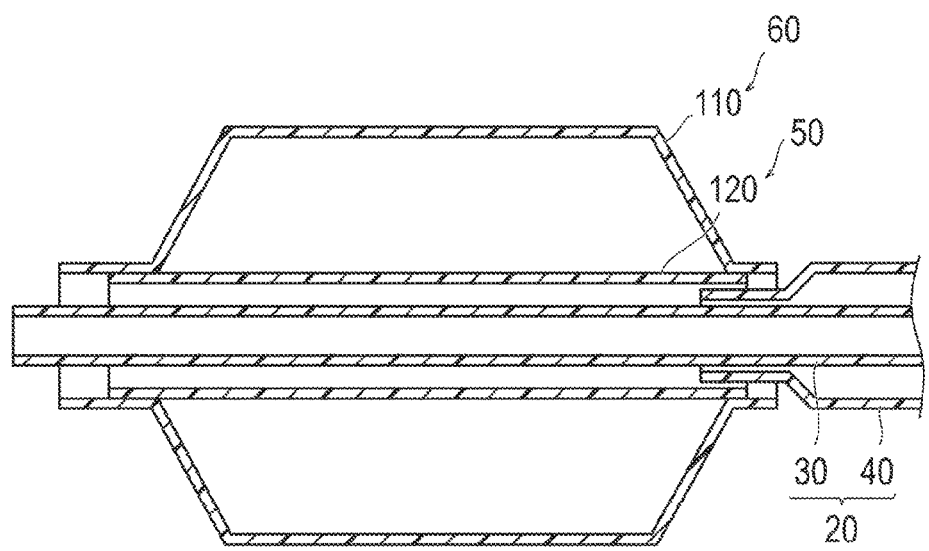
FIG. 12 is a cross-sectional view for describing the manufacturing method of the balloon catheter according to the embodiment.

As illustrated in FIG. 12, the membranous material 50 is arranged on an inner side of the balloon 60, and the distal portion of the shaft assembly 20 is inserted into the membranous material 50. Then, the balloon 60 and the membranous material 50 are joined to an outer peripheral surface of the shaft assembly 20. The joining is performed in this way in a state where the distal portion of the shaft assembly 20 is arranged on the inner side of the balloon 60 and on the inner side of the membranous material 50. Accordingly, the respective members can be joined to each other. Therefore, the assembly work can be relatively simply and easily carried out. Details of the manufacturing operation of the balloon catheter 10 will be described in more detail later.

In addition, in the balloon catheter 10, a position of a proximal portion 59 of the membranous material 50 and a position of a proximal portion 69 of the balloon 60 are adjusted so that the fluid flowing into the space portion 51 does not leak out from the space portion 51. Specifically, as illustrated in FIG. 4, the proximal portion 59 of the membranous material 50 is fixed to an outer peripheral surface of the distal portion 45 of the outer shaft 40. On the other hand, the proximal portion 69 of the balloon 60 is fixed to the outer peripheral surface of the outer shaft 40 at a position on the proximal side in the axial direction relative to the proximal portion 59 of the membranous material 50. According to this arrangement, the proximal portion 59 of the membranous material 50 is covered by the proximal portion 69 of the balloon 60. Therefore, it is possible to preferably prevent the fluid from leaking out from a portion between the membranous material 50 and the outer shaft 40.

Next, a configuration of the inner shaft 30 will be described.

As illustrated in FIG. 2, for example, the inner shaft 30 can be configured to have a first portion 35 which is located on the distal side, a second portion 36 which is connected to the first portion 35 and which is located on the proximal side relative to the first portion 35, and a third portion 37 which is connected to the second portion 36 and which is located on the proximal side relative to the second portion 36. In the balloon catheter 10, the contracting and transforming portion which partially contracts and transforms the inner shaft 30 when the internal pressure in the space portion 51 increases is configured to include the second portion 36.

It is preferable to adopt a configuration in which the first portion 35 of the inner shaft does not buckle, even if the first portion 35 abuts living body organs, when the balloon catheter 10 is operated to move inside the living body organs. In addition, it is preferable to adopt a configuration in which the first portion 35 is very flexible so that the overall balloon catheter 10 can smoothly move along a curved pathway or the like inside the living body organs. Therefore, for example, the first portion 35 can be configured so as to be stronger against buckling and more flexible than the second portion 36 or the third portion 37.

The second portion 36 of the inner shaft 30 possesses a configuration in which the second portion 36 is contracted so as to collapse, for example, when internal pressure in the space portion 51 increases up to a predetermined magnitude, and in which the second portion 36 restores its original shape from the contracted state, when the internal pressure in the space portion 51 decreases to a predetermined magnitude. In addition, when the guidewire 200 slides in the second portion 36 in a state where the contracted second portion 36 is in pressing contact with the guidewire 200, it is preferable that the second portion 36 has sufficient buckling strength that the second portion 36 does not buckle due to the sliding. The length of the second portion 36 is shorter than the length of the membranous material 50 in the axial direction. However, in view of a relationship with the space portion 51, the length or the position of the second portion 36 in the axial direction can be changed so long as the second portion 36 can be contracted in the presence of an increase in the internal pressure in the space portion 51. However, it is preferable to form the second portion 36 at a position other than the distal portion of the inner shaft 30 so that the second portion 36 does not cause the inner shaft 30 to buckle.

A configuration can be adopted in which the third portion 37 of the inner shaft 30 is provided with stiffness which enables the third portion 37 to transmit pushing force to the distal side of the balloon catheter 10, and in which the third portion 37 is provided with pressure resistance strength against the fluid flowing into the fluid lumen 41 and the space portion 51. In addition to this configuration, it is preferable to adopt a configuration of providing improved sliding performance between the third portion 37 and the guidewire 200.

For example, the inner shaft 30 is configured so that the first portion 35, the second portion 36, and the third portion 37 are respectively combined with a separate member having the above-described characteristics. Since the inner shaft 30 configured in this way is used, it is possible to improve a function of the balloon catheter 10 provided in order to allow smooth movement inside the living body organs and to improve insertion capability into the stenosis or the like. However, the inner shaft 30 may be configured so that at least a portion can be contracted as a result of the increase in the internal pressure in the space portion 51.

A contrast marker 39 can be disposed on the inner shaft 30, specifically the outer peripheral surface of the inner shaft 30. For example, the contrast marker 39 can be configured so that an X-ray opaque marker is attached to the outer surface of the inner shaft 30. Examples of the contrast marker 39 include Pt, Pt alloy, W, W alloy, Ag, Ag alloy, or the like. In addition, for example, a distal tip or the like for preventing the living body organs from being damaged when the distal end of the balloon catheter 10 and the living body organs come into contact with each other can be disposed in the distal end of the inner shaft 40.

Examples of materials forming the inner shaft 30 include polyolefin such as polyethylene, polypropylene, ethylene-propylene copolymer and the like, ethylene-vinyl acetate copolymer and the like, thermoplastic resin such as soft poly vinyl chloride and the like, various rubber materials such as silicone rubber, latex rubber, and the like, various elastomers such as polyurethane elastomer, polyamide elastomer, polyester elastomer, and the like, or crystalline plastics such as polyamide, crystalline polyethylene, crystalline polypropylene, and the like. For example, an antithrombotic substance such as heparin, prostaglandin, urokinase, an arginine derivative, and the like is blended in the above-describe materials so as to obtain a material having antithrombotic properties. For example, when the first portion 35, the second portion 36, and the third portion 37 of the inner shaft 30 are respectively configured as separate members, it is possible to appropriately select one corresponding to its function from the above-described respective materials.

The material constituting the outer shaft 50 can be one of the materials described above for the inner shaft 30. In addition, a portion (for example, outer surface of the outer shaft) which comes into contact with the blood on the outer shaft 50 can be coated with a substance having the antithrombotic properties.

Next, a configuration of the balloon 60 will be described.

The balloon 60 inflates and deflates, since an internal volume of the balloon increases and decreases due to a change in pressure in the lumen 61. As illustrated in FIG. 9, the balloon 60 has an inflatable portion 63 which can inflate in a cylindrical shape, a distal side conical portion 64 which is located on the distal side relative to the inflatable portion 63, and a proximal side conical portion 65 which is located on the further proximal side relative to the inflatable portion 63. When a stenosis is expanded using the balloon catheter 10, the balloon 60 is inflated in a state where the inflatable portion 63 is located in the stenosis, and a pressing force is applied to the stenosis via inflation and expansion of the inflatable portion 63.

Figure 6:
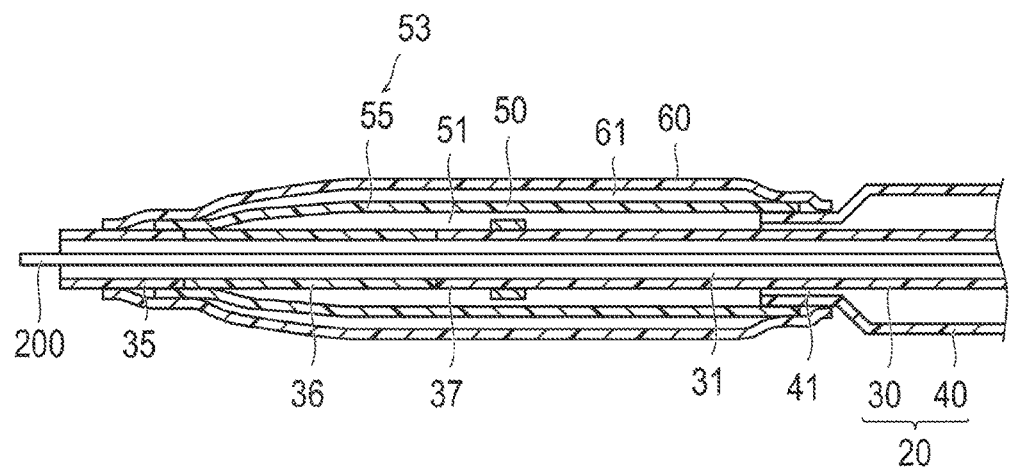
FIG. 6 is a cross-sectional view for describing an operation of the balloon catheter according to the embodiment.

When the balloon catheter 10 is introduced into a living body, as illustrated in FIG. 6, the introduction can be performed in a state where the balloon 60 is deflated or collapsed and the balloon 60 is folded around the outer surface of the inner shaft 30. The folding method or the folding form can be conventional methods or forms which are used for the balloon catheter in the medical field.

As materials forming the balloon 60, it is preferable to use materials which are flexible to some degree and are rigid to such an extent as to be capable of feeding the blood. Examples of materials include polyolefin such as polyethylene, polypropylene, ethylene-propylene copolymer, and the like, polyester such as polyethylene terephthalate and the like, thermoplastic resin such as poly vinyl chloride, ethylene-vinyl acetate copolymer, cross-linked ethylene-vinyl acetate copolymer, polyurethane, and the like, polyamide, polyamide elastomer, silicone rubber, latex rubber, or the like. The balloon 60 can be formed so as to have a single layer structure using these materials, or can be formed so as to have a laminate structure of two or more layers. In a manner similar to the outer shaft 40, the balloon 60 can be coated with a substance having antithrombotic properties. As will be described later, in a step of manufacturing the balloon catheter 10, the balloon 60 is prepared in a form of a hollow tube material (refer to FIG. 11).

As the fluid used in inflating the balloon 60, either liquid or gas may be used. For example, the fluid includes gas such as helium gas, $CO_2$ gas, $O_2$ gas, and the like, or liquid such as a physiological slat solution, a contrast agent, and the like.

Next, a configuration of the membranous material 50 will be described.

As illustrated in FIG. 2, for example, the membranous material 50 can be configured to include a thin film-shaped member which is flexible. In addition, the ejection portion 53 disposed in the membranous material 50 can be configured to include a fragile portion 55 which forms the opening 57 in a portion of the membranous material 50, for example, when the internal pressure in the space portion 51 increases up to a predetermined magnitude (refer to FIG. 8).

Figure 5:
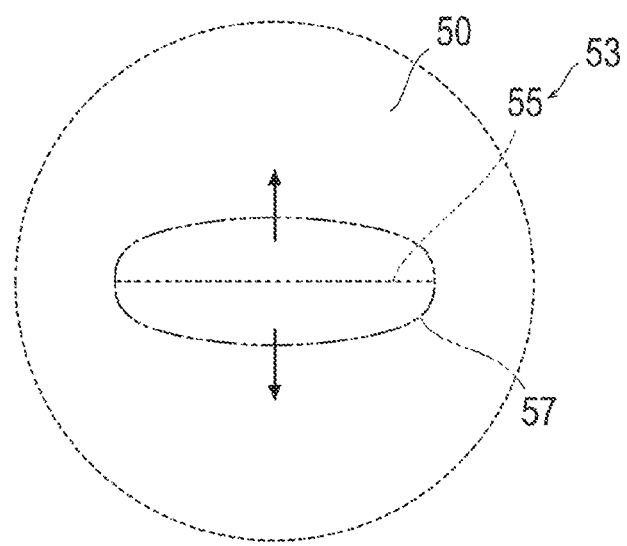
FIG. 5 is an enlarged view illustrating a fragile portion when viewed in a direction of an arrow 5 illustrated in FIG. 2.

As illustrated in FIG. 5, the fragile portion 55 can be configured so that the opening 57 is formed by rupturing or breaking a part of the membranous material 50 over a predetermined range or distance in the axial direction. It is possible to reliably define a portion which starts to be ruptured in the membranous material 50 by disposing the fragile portion 55 in the membranous material 50. As a method of forming the fragile portion 55, for example, it is possible to employ a method of thinning a part of the membranous material 50, a method of applying heat or the like so that the membranous material 50 is likely to be partially ruptured, a method of forming a cut line so that the membranous material 50 is likely to be partially ruptured, or the like. It is thus understood that the fragile portion 55 is weaker than, or more easily ruptured/broken, than the portion of the membranous material 50 surrounding the fragile portion 55.

As illustrated in FIGS. 8 and 9, a fluid (illustrated by an arrow f in FIG. 8) flowing out from the opening 57 formed by rupturing the membranous material 50 flows into the lumen 61 of the balloon 60. Then, as the fluid flows into the lumen 61, the balloon 60 rapidly inflates.

It is preferable to set the internal pressure in the space portion 51 when the membranous material 50 is ruptured so that an excessive pressing force is not applied to an inner wall or the like in the blood vessel around the stenosis. In addition, in order that pressure which is small enough not to rupture the membranous material 50 brings the second portion 36 of the inner shaft 30 into pressing contact with the guidewire 200, for example, the various pressures for operating the balloon catheter 10 can be set as follows.

Pressure A in the space portion 51 (pressure when the second portion 36 of the inner shaft 30 comes into pressing contact with the guidewire 200)<pressure B in the space portion 51 (pressure when the fragile portion 55 is ruptured, for example, 5 atm)≤pressure C (pressure resistance in the balloon 60, approximately the same as that of the balloon included in the conventional balloon catheter).

For example, the fragile portion 55 can be configured so that a flow rate of the fluid flowing from the space portion 51 increases with the lapse of time and the ruptured portion of the membranous material 50 gradually increases. According to this configuration, it is possible to decrease a possibility that the rapidly inflated balloon 60 may influence the living body organs. In this case, in order to prevent the fluid from staying inside the space portion 41, it is preferable to dispose the fragile portion 55 so as to form the opening 57 which has a predetermined length along the axial direction as illustrated in FIG. 5.

The ejection portion 53 included in the membranous material 50 may be configured so that the fluid can flow into the lumen 61 of the balloon 60 from the space portion 51 when the internal pressure in the space portion 51 increases up to predetermined pressure, and is not limited only to a form as in the fragile portion 55 illustrated in FIG. 5. For example, a configuration can be adopted in which a hole which can function as the ejection portion 53 is formed in the membranous material in advance so that the fluid can flow out from the hole when the internal pressure reaches the predetermined pressure, or the ejection portion 53 can be configured by disposing a member functioning as a one-way valve in the membranous material 50. In addition, the number of the ejection portions or a position of the ejection portion(s) can also be changed depending on product specifications.

Examples of materials for forming the membranous material 50 preferably include a low compliance material used for the balloon of the conventional balloon catheter, and the material includes nylon, polyimide, PET, or the like. Using the low compliance material can prevent the membranous material 50 from excessively expanding when the internal pressure in the space portion 51 increases. However, without being limited to the above-described materials, any material may be used as long as the material can be processed in a membranous shape and the ejection portion 53 can be formed. For example, it is possible to use the materials like those described above for the balloon 60. As will be described later, in a step of manufacturing the balloon catheter 10, the membranous material 50 is prepared in a form of a hollow tube material (refer to FIG. 11).

In addition, it is preferable to install the membranous material 50 so that an outer shape as a product does not become excessively large in a state where the balloon 60 is deflated, and so that a clearance is not made between the inner shaft 30 and the balloon 60 if possible, within a range which does not influence the folding of the balloon 60 or the outer shape of the balloon 60.

Next, referring to FIGS. 6 to 9, an operation of the balloon catheter 10 according to the present embodiment will be described.

When procedures are required to expand a stenosis by using the balloon catheter 10, the guidewire 200 and the balloon catheter 10 are introduced into living body organs.

As illustrated in FIG. 6, the balloon catheter 10 is moved while being guided by the guidewire 200 which is introduced ahead of the balloon catheter 10. At this time, the guidewire 200 is inserted into the guidewire lumen 31 in the inner shaft 30.

The guidewire 200 used together with the balloon catheter 10 can be a conventional guidewire used in the medical field. For example, those which are configured so that an elongated wire made of a super-elastic alloy such as a nickel-titanium alloy, a copper-zinc alloy, and the like, a metal material such as stainless steel and the like, a resin material having relatively high rigidity, or the like is coated with a resin material such as polyvinyl chloride, polyethylene, polypropylene, ethylene-propylene copolymer, and the like are used as the guidewire 200.

Figure 7:
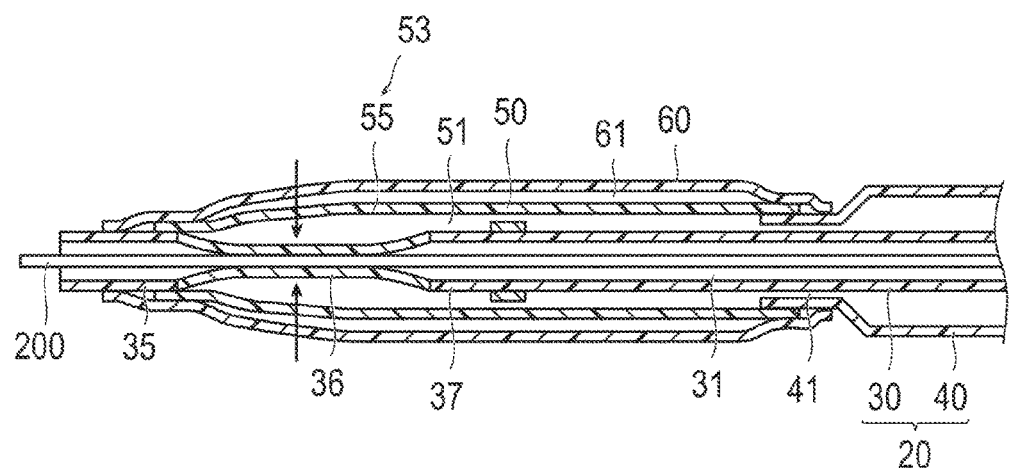
FIG. 7 is a cross-sectional view for describing an operation of the balloon catheter according to the embodiment.

When the balloon catheter 10 is moved inside the living body organs, if for example the movement of the balloon catheter 10 is hindered since the stenosis or the like is present on the distal side, the fluid is supplied to the space portion 51 from a fluid supply source which serves as an external device. Then, as illustrated in FIG. 7, the second portion 36 of the inner shaft 30 is contracted, and is brought into pressing contact with the guidewire 200. When an operator's hand pushes and pulls the balloon catheter 10 in a state where the inner shaft 30 is in pressing contact with the guidewire 200, the balloon catheter 10 is moved integrally with the guidewire 200. Therefore, in a state where trackability and pushability of the balloon catheter 10 are improved by the guidewire 200, the balloon catheter 10 can be moved. As a result, the balloon 60 can be more easily inserted into the stenosis or the like.

Thereafter, if the inflatable portion 63 of the balloon 60 is located in the stenosis and the fluid is further supplied to the space portion 51, as illustrated in FIG. 8, the opening 57 is formed after the fragile portion 55 starts to be ruptured in the membranous material 50.

Then, as illustrated in FIG. 9, the fluid flows into the lumen 61 of the balloon 60 through the opening 57 formed in the membranous material 50, thereby inflating the balloon 60. As a result, a pressing force is applied to the stenosis via the inflatable portion 63 of the balloon 60, thereby spreading out the stenosis.

In the procedures using the balloon catheter 10, in addition to when work for inserting the balloon 60 into the stenosis is carried out, for example, when the movement to the distal side or in the distal direction is likely to be hindered by various obstacles or the like, the fluid is caused to flow into the space portion 51, and the inner shaft 30 is suitably brought into pressing contact with the guidewire 200. In this manner, trackability and pushability of the balloon catheter 10 are improved. Moreover, it is possible to perform an operation such as the movement of the balloon catheter 10 and the like. In addition, after the fluid is caused to flow into the space portion 51 once, the fluid is discharged from the space portion 51. In this manner, it is possible to release a state where the inner shaft 30 and the guidewire 200 are in pressing contact with each other.

As described above, according to the balloon catheter 10 of the present embodiment, the inner shaft 30 is contracted, and is brought into pressing contact with the guidewire 200. In this manner, the balloon catheter 10 is able to perform forward and rearward movement or the like in a state where trackability and pushability of the balloon catheter 10 are improved. In addition, the balloon catheter 10 can be smoothly moved along the living body organs or the like by releasing a state where the inner shaft 30 is in pressing contact with the guidewire 200. Furthermore, it is possible to cause the fluid to flow into the lumen 61 of the balloon 60 from the space portion 51 by increasing the internal pressure in the space portion 51 up to the predetermined pressure. Accordingly, it is possible to perform various operations such as pressing contact between the inner shaft 30 and the guidewire 200, releasing the pressing contact, and inflating the balloon 60, by adjusting a flow rate of the fluid which is caused to flow into the space portion 51.

In addition, the distal portion 45 of the outer shaft 40 covers the inner shaft 30 within a predetermined range or over a predetermined distance in the axial direction, the proximal portion 58 of the membranous material 50 is arranged on the outer periphery of the distal portion 45 of the outer shaft 40, and the proximal portion 68 of the balloon 60 is arranged on the outer periphery of the proximal portion 58 of the membranous material 50. Therefore, it is possible to relatively simply and easily carry out assembly of the balloon catheter 10. As illustrated, the proximal-most portion of the membranous 50 is positioned outwardly of and in axial overlapping relation to the outer periphery of the distal-most portion of the outer shaft 30, the proximal-most portion of the balloon 60 is positioned outwardly of and in axial overlapping relation to the outer periphery of the proximal-most portion of the membranous material 50, and the proximal-most end of the balloon 60 is proximal of the proximal-most end of the membranous material 50.

In addition, a configuration is adopted in which the proximal portion 59 of the membranous material 50 is covered by the proximal portion 69 of the balloon 60. Accordingly, it is possible to preferably prevent the fluid from leaking out from the proximal portion 59 of the membranous material 50.

In addition, the opening 57 is formed in the membranous material 50 over the relatively wide range along the axial direction by the fragile portion 55 included in the membranous material 50. Accordingly, the fluid can rather smoothly flow into the lumen 61 of the balloon 60 from the space portion 51, and thus it is possible to preferably prevent the fluid from staying inside the space portion 51 after the fluid flows out therefrom.

Next, a manufacturing method of the balloon catheter 10 according to the above-described embodiment will be described.

The manufacturing method described hereinafter is a method of manufacturing the balloon catheter 10 which is configured to include the inner shaft 30 into which the guidewire 200 is inserted, the outer shaft 40 that partitions or defines a boundary of the fluid lumen 41 for injecting or introducing the fluid in a space between the outer periphery of the inner shaft 30 and the inner periphery of the outer shaft 40, the membranous material 50 that defines the space portion 51 located outwardly of the outer periphery on the distal portion of the inner shaft 30, and that includes the ejection portion 53 causing the fluid to flow out from the space portion 51 in response to the increase in the internal pressure in the space portion 51, and the balloon 60 whose lumen 61 is formed on the outer periphery of the membranous material 50, in which at least a part of the inner shaft 30 is transformable or deformable so as to contract radially inward in response to the increase in the internal pressure in the space portion 51.

Figure 10:
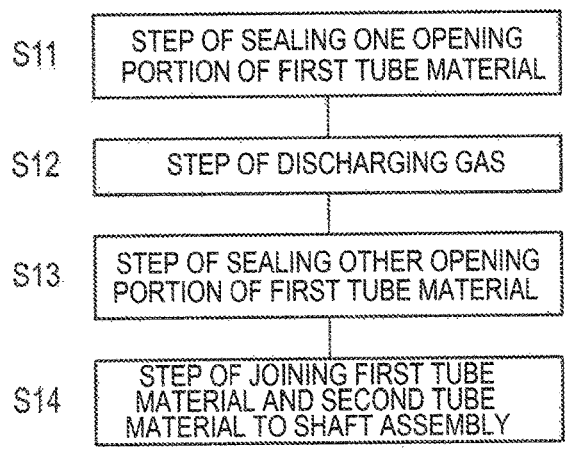
FIG. 10 is a flowchart illustrating each step in a manufacturing method of the balloon catheter according to the embodiment.
Figure 11:
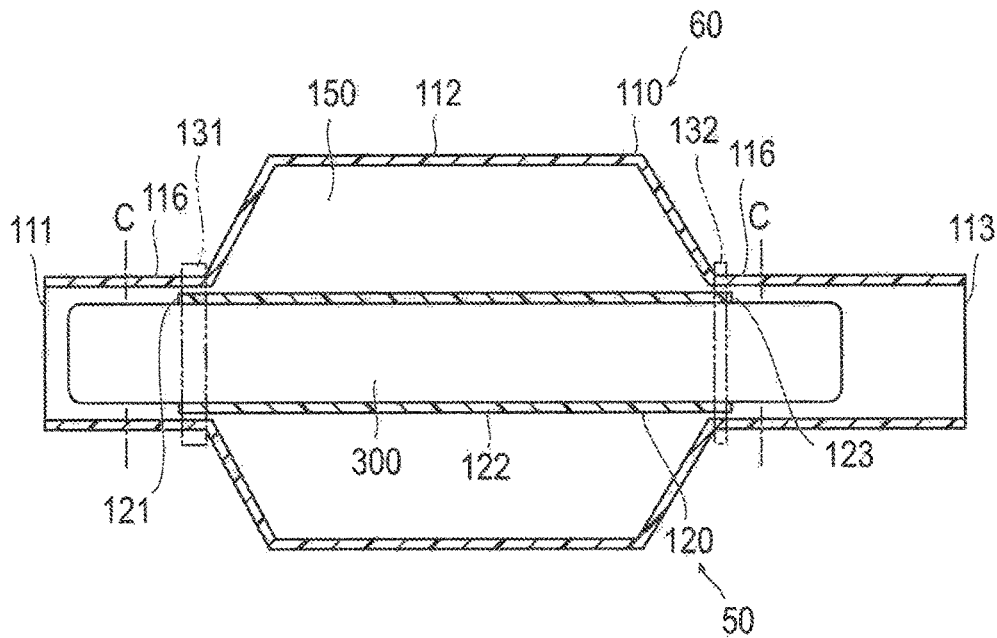
FIG. 11 is a cross-sectional view for describing the manufacturing method of the balloon catheter according to the embodiment.

As illustrated in FIGS. 10 to 12, the above-described manufacturing method includes a step (S11) of sealing one opening portion between a distal opening portion 111 and a proximal opening portion 113 of a first tube material 110 (forming the balloon 60) in a state where a second tube material 120 forming the membranous material 50 is inserted into or positioned in the first tube material 110, a step (S12) of discharging gas between the first tube material 110 and the second tube material 120 via the other opening portion which is not sealed in the first tube material 110, a step (S13) of sealing the other opening portion of the first tube material 110, and a step (S14) of joining the first tube material 110 and the second tube material 120 to the shaft assembly 20 which includes the inner shaft 30 and the outer shaft 40. Hereinafter, each step will be described in more detail.

As illustrated in FIG. 11, when the balloon catheter 10 is manufactured, the balloon 60 is prepared as the first tube material 110 which is configured or fabricated from the previously exemplified material or the like. The first tube material includes a distal opening 111 located on the distal side, a main body portion 112 forming the inflatable portion 63 and the respective conical portions 64 and 65, and a proximal opening 113 located on the proximal side.

The membranous material 50 is prepared as the second tube material 120 which is configured or fabricated from the previously exemplified material or the like. The second tube material 120 includes a distal opening 121 located on the distal side, a main body portion 122 having a straight body shape, and a proximal opening 123 located on the proximal side.

As illustrated in FIG. 11, a metal core 300 is first inserted into the second tube material 120. Then, the first tube material 110 is arranged to cover in an axially overlapping manner the second tube material 120. In this manner, the second tube material 120 is in a state of being inserted into or positioned in the first tube material 110. As the metal core 300, it is possible to use a conventional metal core which is used in manufacturing the balloon catheter 10, for example.

Next, the distal opening 111 of the first tube material 110 is sealed, thereby forming a first sealing portion 131 at which the distal portion of the first tube material 110 is sealed to the second tube material 120. By forming the first sealing portion 131, a predetermined space 150 which communicates with the proximal opening 113 of the first tube material 110 is partitioned between the first tube material 110 and the second tube material 120 (i.e., between the outer peripheral surface of the second tube material 120 and the inner peripheral surface of the first tube material 110). For example, the sealing can be performed by fusing the first tube material 110 to the second tube material 120. The fusing method can employ ultrasound heating, induction heating using a coil, or the like. The sealing can be performed by using a method other than fusion, for example, by adhesion or the like.

Next, gas (for example, air) between the first tube material 110 and the second tube material 120 is discharged or drawn out via the proximal opening 113 of the first tube material 110. The gas discharging can be performed by utilizing a conventional suction device such as a suction pump and the like. In order to facilitate an understanding here, the illustrated predetermined space 150 is exaggerated in the drawing as if the predetermined space 150 is present even after the gas discharging. However, the gas discharging causes the main body portion 112 of the first tube material 110 to be drawn towards and stick to the main body portion 122 of the second tube material 120. Accordingly, the predetermined space 150 is contracted.

Next, the proximal opening 113 of the first tube material 110 is sealed, thereby forming a second sealing portion 132 at which the proximal portion of the first tube material 110 is sealed to the second tube material 120. The method employed to seal the proximal opening 113 can be a method which is the same as the method of sealing the distal opening 111. In an alternative possibility in which the proximal opening 113 of the first tube material 110 is first sealed before the distal opening, a gas discharging step is performed. Thereafter, a step of sealing the distal opening 111 of the first tube material 110 may be performed.

Next, a portion which is unnecessary for a product is appropriately cut from the first tube material 110. For example, the cutting is performed along a cut line c which is set in each portion on the distal side and the proximal side of the first tube material 110. For example, as illustrated in FIG. 5, the cutting can be performed at a position where an excessive portion 116 is located on each of the distal side and the proximal side of the first tube material 110 so that the proximal portion 59 of the second tube material 120 forming the membranous material 50 can be covered with the proximal portion 69 of the first tube material 110 forming the balloon 60.

Next, as illustrated in FIG. 12, the first tube material 110 and the second tube material 120 are joined to the shaft assembly 20 including the inner shaft 30 and the outer shaft 40. The joining method can employ a conventional method in view of the respective tube materials 110 and 120 and the material of the respective shafts 30 and 40. For example, the joining can be performed using a method such as ultrasound heating, induction heating using a coil, adhesion, and the like. The shaft assembly 20 and the hub 70 may be connected to each other after the respective tube materials 110 and 120 are joined to the shaft assembly 20, or may be connected to each other before the joining therebetween.

Through the above-described procedure, it is possible to manufacture the balloon catheter 10 whose configuration members are the first tube material 110 forming the balloon 60 in which the lumen 61 is formed on the outer periphery of the membranous material 50 and the second tube material 120 forming the membranous material 50 in which the space portion 51 into which the fluid can flow is partitioned on the outer periphery of the inner shaft 30.

Next, a modification example of the manufacturing method of the above-described balloon catheter 10 will be described.

Figure 13:
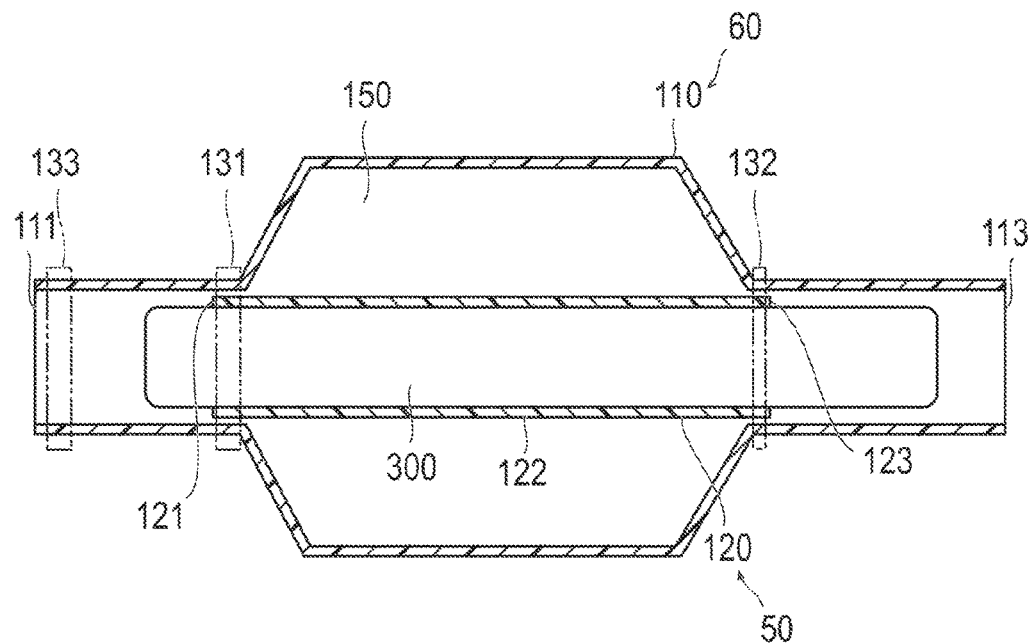
FIG. 13 is a cross-sectional view for describing a modification example of the manufacturing method of the balloon catheter according to the embodiment.

The step (S12) of discharging the gas between the first tube material 110 and the second tube material 120 can be performed when either the distal opening 111 or the proximal opening 113 of the first tube material 110 is sealed. Therefore, for example, as illustrated in FIG. 13, without fusing the first tube material 110 and the second tube material 120 to each other, the gas discharging can be performed in a state where another sealing portion 133 for sealing the distal opening 111 of the first tube material 110 is formed. The sealing portion 133 can be formed by fusing or adhesion of the first tube material 110.

After the sealing portion 133 is formed, similarly to the previously described procedure, the gas is discharged via the proximal opening 113 of the first tube material 110. Thereafter, the first tube material 110 and the second tube material 120 are fused to each other in a portion corresponding to the first sealing portion 131, a portion corresponding to the second sealing portion 132, and the like. The fusing order may start from any portion of the portion corresponding to the first sealing portion 110 and the portion corresponding to the second sealing portion 120. Then, the balloon catheter 10 can be manufactured by joining the respective tube materials 110 and 120 to the shaft assembly 20.

The detailed description above describes a balloon catheter and manufacturing method, and modifications, representing examples of the inventive balloon catheter and manufacturing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
   an inner shaft that includes a guidewire lumen configured to receive a guidewire so that the balloon catheter can be guided along the guidewire;
   an outer shaft that forms, together with the inner shaft, a fluid lumen into which a fluid is to be introduced;
   a membranous material that defines, together with the inner shaft, a space portion located outwardly of an outer periphery of a distal portion of the inner shaft;
   an inflatable and deflatable balloon in which a lumen is formed, the balloon being located outwardly of an outer periphery of the membranous material;
   the membranous material including an ejection portion which permits the fluid in the space portion to flow into the lumen of the balloon when an internal pressure in the space portion increases to a predetermined pressure as the fluid flows into the space portion; and
   the inner shaft including a contracting and transforming portion which transforms at least a portion of the inner shaft so as to contract radially inward in response to an increase in the internal pressure in the space portion.

2. The balloon catheter according to claim 1,
   wherein a distal portion of the outer shaft covers the inner shaft within a predetermined range in an axial direction,
   wherein a proximal-most portion of the membranous material is positioned outwardly of and in axial overlapping relation to an outer periphery of a distal-most portion of the outer shaft, and
   wherein a proximal-most portion of the balloon is positioned outwardly of and in axial overlapping relation to an outer periphery of the proximal-most portion of the membranous material.

3. The balloon catheter according to claim 2,
   wherein a proximal portion of the membranous material is fixed to an outer peripheral surface of a distal portion of the outer shaft, and wherein a proximal portion of the balloon is fixed to an outer peripheral surface of the outer shaft at a position proximal of the proximal-most portion of the membranous material.

4. The balloon catheter according to claim 3, wherein the ejection portion includes a fragile portion which forms an opening in the membranous material by rupturing a portion of the membranous material over a predetermined range in an axial direction.

5. The balloon catheter according to claim 1,
wherein the membranous material possesses a proximal portion fixed to an outer peripheral surface of a distal portion of the outer shaft, and
wherein the balloon possesses a proximal portion fixed to an outer peripheral surface of the outer shaft at a position proximal of a proximal-most portion of the membranous material.

6. The balloon catheter according to claim 1, wherein the ejection portion includes a fragile portion which forms an opening in the membranous material by rupturing a portion of the membranous material over a predetermined range in an axial direction.

7. The balloon catheter according to claim 1, wherein the balloon possesses a distal portion fixed to an outer periphery of the inner shaft and a proximal portion fixed to an outer periphery of the outer shaft.

8. The balloon catheter according to claim 7, wherein the membranous material possesses a distal portion fixed to an outer periphery of the inner shaft and a proximal portion fixed to an outer periphery of the outer shaft.

9. The balloon catheter according to claim 1, wherein the membranous material possesses a distal portion fixed to an outer periphery of the inner shaft and a proximal portion fixed to an outer periphery of the outer shaft.

10. A method of manufacturing a balloon catheter, the balloon catheter including an inner shaft into which a guidewire is insertable, an outer shaft positioned outwardly of on an outer periphery of the inner shaft, a membranous material positioned outwardly of an outer periphery of a distal portion of the inner shaft to form a space portion between the distal portion of the inner shaft and the membranous material, and a balloon positioned outwardly of an outer periphery of the membranous material to define a lumen between the balloon and the membranous material, at least a part of the inner shaft being transformable so as to contract radially inward in response to an increase in internal pressure in the space portion, the method comprising:
sealing one opening portion of a first tube material in a state in which a second tube material forming the membranous material is positioned inside the first tube material forming the balloon, the one opening portion of the first tube material being either a proximal opening portion at a proximal end of the first tube material or a distal opening portion at a distal end of the first tube material, the first tube material possessing an other opening portion at an end of the first tube opposite to the one opening portion;
discharging gas between the first tube material and the second tube material via the other opening portion which is not sealed;
sealing the other opening portion of the first tube material; and
joining the first tube material and the second tube material to a shaft assembly which includes the inner shaft and the outer shaft.

11. The method according to claim 10, further comprising inserting a metal core into the second tube material before sealing the one opening portion of the first tube material.

12. The method according to claim 10, wherein the discharging of the gas between the first tube material and the second tube material via the other opening portion is performed by suction.

13. A method of using a balloon catheter comprising
inserting a balloon catheter into a living body organ, the balloon catheter comprising: an inner shaft that includes a guidewire lumen, an outer shaft positioned outwardly of the inner shaft, a membranous material positioned outwardly of the inner shaft, and an inflatable and deflatable balloon located outwardly of the membranous material, the membranous material possessing an inner peripheral surface and the inner shaft possessing an outer peripheral surface;
moving the balloon catheter in the living body organ by guiding the balloon catheter along a guidewire located in the guidewire lumen to move the balloon catheter relative to the guidewire within the living body organ;
introducing fluid into a space between the outer peripheral surface of the inner shaft and the inner peripheral surface of the membranous material to cause a portion of the inner shaft to deform inwardly into contact with the guidewire in the guidewire lumen so that the guidewire and the balloon catheter move together as a unit;
moving the balloon catheter while the portion of the inner shaft is in contact with the guidewire to move the guidewire and the balloon catheter together and position the balloon catheter at a stenosis; and
inflating the balloon into contact with the stenosis to spread out the stenosis.

14. The method according to claim 13, wherein the inflation of the balloon comprises the fluid in the space between the outer peripheral surface of the inner shaft and the inner peripheral surface of the membranous material applying a force to a fragile portion of the membranous material causing the fragile portion to open and communicate the space with a lumen between the balloon and the membranous material so that the fluid in the space flows into the lumen between the balloon and the membranous material.

15. The method according to claim 14, wherein the portion of the inner shaft deforms inwardly into contact with the guidewire before the fragile portion is opened.

* * * * *